United States Patent [19]

Dralle-Voss et al.

[11] Patent Number: 5,872,149
[45] Date of Patent: Feb. 16, 1999

[54] ALK(EN)YLDICARBOXYLIC ACID BISESTERS, THEIR USE, AND PROCESSES FOR THEIR PREPARATION

[75] Inventors: Gabriele Dralle-Voss, Darmstadt; Günter Oetter, Frankenthal; Hans-Ulrich Wekel, Ellerstadt; Knut Oppenländer, Ludwigshafen, all of Germany

[73] Assignee: BASF Aktiengesellschaft, Ludwigshafen, Germany

[21] Appl. No.: 894,155

[22] PCT Filed: Feb. 15, 1996

[86] PCT No.: PCT/EP96/00657

§ 371 Date: Aug. 15, 1997

§ 102(e) Date: Aug. 15, 1997

[87] PCT Pub. No.: WO96/25384

PCT Pub. Date: Aug. 22, 1996

[30] Foreign Application Priority Data

Feb. 15, 1995 [DE] Germany .................. 19 505 100.9

[51] Int. Cl.⁶ .................................................. A61K 31/235
[52] U.S. Cl. .................. 514/533; 504/313; 426/654; 510/505; 510/513; 514/937; 554/223; 554/224; 554/148
[58] Field of Search .......................... 504/313; 426/654; 510/505, 513; 514/533, 937; 554/223, 224, 148

[56] References Cited

U.S. PATENT DOCUMENTS

| | | |
|---|---|---|
| 2,650,211 | 8/1953 | Dannenberg et al. . |
| 4,159,958 | 7/1979 | de Vries . |
| 4,234,435 | 11/1980 | Meinhardt et al. . |

FOREIGN PATENT DOCUMENTS

| | | |
|---|---|---|
| 898 441 | of 0000 | Belgium . |
| 0 107 199 | 10/1980 | European Pat. Off. . |
| 163 348 | of 0000 | Germany . |
| 40 624 | 8/1965 | Germany . |
| 42 38 032 | 11/1992 | Germany . |
| 05125014 | of 0000 | Japan . |
| 5 7065 -793 | of 0000 | Japan . |
| 6 0018 584 A | of 0000 | Japan . |
| 432 172 | of 0000 | U.S.S.R. . |
| 457 754 | of 0000 | U.S.S.R. . |
| WO 94/0050 | 1/1994 | WIPO . |

*Primary Examiner*—Samuel Barts
*Attorney, Agent, or Firm*—Oblon, Spivak, McClelland, Maier & Neustadt, P.C.

[57] ABSTRACT

The present invention relates to monomeric, oligomeric and polymeric bisesters of alkyl- or alkenyldicarboxylic acid derivatives and polyalcohols, and their use as solubilizers, emulsifiers and/or detergents. In particular, the bisesters are advantageously used in cosmetic compositions, detergents and cleaners, pharmaceutical compositions, foodstuffs and crop protection compositions. The invention furthermore relates to a process for preparing these bisesters.

20 Claims, No Drawings

ALK(EN)YLDICARBOXYLIC ACID BISESTERS, THEIR USE, AND PROCESSES FOR THEIR PREPARATION

This application is a 371 of PCT/EP96/00657 filed Feb. 15, 1996.

I. SUBJECT OF THE INVENTION

The present invention relates to monomeric, oligomeric and polymeric bisesters of alkyl- or alkenyldicarboxylic acid derivatives and polyalcohols, and their use as solubilizers, emulsifiers and/or detergents. In particular, the bisesters are advantageously used in cosmetic compositions, detergents and cleaners, pharmaceutical compositions, foodstuffs and crop protection compositions. The invention furthermore relates to a process for preparing these bisesters.

I. BACKGROUND OF THE INVENTION

In the surfactant and emulsifiers sector, in recent years nonionic surface-active substances which are readily biodegradable, have a low toxicity and thus possess good environmental compatibility have increasingly come to the fore.

An important group of nonionic compounds of this type are esters of fatty acids and polyalcohols, such as sucrose esters, sorbitan esters and glycerol and polyglycerol fatty acid esters. In these compounds a polyalcohol group is esterified with a hydrophobic fatty acid radical.

Most products of the classes of compound mentioned are too nonpolar to be employed in aqueous formulations as a surfactant. The more hydrophilic products of this compound type prove in some properties such as foaming and wetting power and the interfacial and surface tension to be still in need of improvement.

JP 051 25 014 discloses monoesters of alkenylcarboxylic anhydrides with hydrophilic compounds, such as polyglycerol, and their use as surfactants.

WO 94/00508 discloses surfactants in which a polyethylene glycol chain is bonded to an alk(en)ylsuccinic acid radical. The polyethylene glycol bisesters described have at least 13 carbon atoms.

DE 42 38 032 discloses bisesters of alk(en)ylsuccinic acid derivatives with polyethylene glycols and their use as skin conditioners.

EP 01 07 199 and BE 898 441 disclose polyoxyalkylenemonoesters of alk(en)ylsuccinic acid derivatives and various intended uses of these compounds.

A disadvantage in these products is in particular the lack of hard water stability and the excessively high interfacial tensions and thus the excessively low solubilizing and emulsifying action.

The use of bisesters of alkyl- or alkenylmalonic acid derivatives, -succinic acid derivatives and -glutaric acid derivatives and polyalcohols which, on the one hand, have a hydrophobic radical and on the other hand at least two polyalcohol components, as solubilizers, emulsifiers or detergents, in particular in detergents, cleaners or personal hygiene compositions, pharmaceutical compositions, foodstuffs or crop protection compositions, has not been described until now.

J 6 00 18 584 discloses alkenylsuccinic acid bisglycerol esters for use as corrosion inhibitors in oil-soluble medium.

In SU 457 754 and in DL 163 348, alkenylsuccinic acid polyglycerol bisesters are employed in electrolytes for silver-plating or for tin baths.

J 5 70 65 793, SU 432 172, U.S. Pat. No. 4,234,435 and U.S. Pat. No. 4,159,958 disclose applications of alkenylsuccinic acid polyglycerol monoesters or bisesters in lubricating oils and cooling lubricants.

DDR 40 624 discloses a process for preparing dicarboxylic acid polyglycerol bisesters and mentions the wetting agent properties of these compounds.

The present invention is based on the object of providing compounds which can be used as detergents, solubilizers and emulsifiers and which do not have the disadvantages described above. The compounds according to the invention should be able to display their advantageous actions, in particular in aqueous or in aqueous/ethanolic systems in which poorly soluble or insoluble substances are to be solubilized or emulsified or from which substances are to be removed with the aid of the detergent activity of the compounds according to the invention.

In particular, the compounds according to the invention should be utilizable in detergents and cleaners and also in cosmetic compositions. The compounds should furthermore be physiologically or phytophysiologically inert in order to be able to employ them in crop protection compositions, pharmaceutical compositions or in dietetic and nondietetic foodstuffs. An advantage in the two last-mentioned application areas would additionally be a low intrinsic odor and a neutral intrinsic taste.

III. DESCRIPTION OF THE INVENTION

The objects are achieved by the mono-, oligo- and polybisesters of malonic acid, succinic acid and glutaric acid derivatives with polyalcohols described in the following and their preparation and use. The bisesters not only have very good detergent, solubilizing and emulsifying properties, but also, compared with the monoesters described, improved stability against water hardness and lower interfacial tensions against various hydrophobic substances, such as, for example, oils. They additionally have a low intrinsic odor and a neutral intrinsic taste.

One object according to the invention is thus a compound of the formula I

where

A is the radical of a monomeric polyalcohol or of an oligomeric polyalcohol which consists of up to 20 monomers linked to one another via ether bonds, the monomeric polyalcohol or the monomer of the oligomeric polyalcohol being an alcohol which has at least 3 carbon atoms and a OH groups;

$a \geq 2$;

O is in each case an oxygen atom of one of the OH groups of the radical A;

X is a radical of the formula II

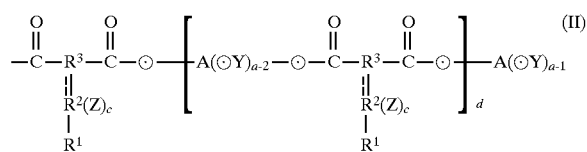

where

A, O and a are as defined above;

Y is a hydrogen atom, or a radical X, which is defined as above;

$R^1$ is a straight-chain or branched alkyl or alkenyl radical having at least 8 carbon atoms;

$R^2$ is a carbon-carbon bond or a straight-chain or branched alkylene or alkenylene radical;

where $R^1$ and $R^2$ together have up to 30 carbon atoms, preferably up to 20 carbon atoms, and preferably 0 to 3 double bonds;

$R^3$ is a methylene, ethylene or n-propylene radical;

= is a single or a double bond;

Z is a radical of the formula III $$\begin{array}{c} O \\ \| \\ C-\odot-A(\odot Y)_{a-1} \\ =R^3 \\ \diagdown \\ C-\odot-A(\odot Y)_{a-1} \\ \| \\ O \end{array} \quad \text{(III)}$$

where

A, O, a, Y and = are as defined above;

c is 0 or 1;

d is an integer $\geq 1$, preferably 1–100, particularly preferably 1–20, very particularly preferably 1–4; and b is an integer which is at least 1 and at most a, which is as defined above;

and whose molecular weight (weight average) is preferably $\leq 100,000$ g/mol, preferably $\leq 50,000$ g/mol and particularly preferably $\leq 20,000$ g/mol.

In the compounds of the formula I, $R^1$ and $R^2$ are preferably together a straight-chain alkyl or an alkenyl radical, and in the case in which = is a double bond, $R^1$ and $R^2$ have no further double bond; and in the case in which = is a single bond, $R^1$ and $R^2$ in total have 1 double bond. Particularly preferably $R^1$ and $R^2$ together contain 8 to 20 carbon atoms.

The preferred radicals for $R^1$ include n-octyl, n-decyl, n-undecyl, n-dodecyl, n-tetradecyl, n-hexadecyl, n-octadecyl, eicosyl, trimeric butenyl, diisobutenyl, tetrameric propenyl, n-octenyl, n-decenyl, n-undecenyl, n-dodecenyl, n-tetradecenyl, n-pentadecenyl, n-hexadecenyl, n-heptadecenyl, n-octadecenyl and eicosenyl, n-octenyl, n-decenyl, n-dodecenyl and n-tetradecenyl being particularly preferred.

$R^2$ is preferably a radical of the formula $R^1\ldots-CH(Z)_1-CH=CH-$ or $R^1\ldots-CH=CH-CH(Z)_1-CH_2-$ $R^1$ and Z being as defined above, and particularly preferably a carbon-carbon bond.

Very particularly preferred compounds are those of the formula IV $$\text{HO}-A-O-\overset{O}{\underset{\|}{C}}-R^3-\overset{O}{\underset{\|}{C}}-O-\left[A(OY)_{a-2}-O-\overset{O}{\underset{\|}{C}}-R^3-\overset{O}{\underset{\|}{C}}-O\right]_d-A-\text{OH} \quad \text{(IV)}$$
$$\begin{array}{cc} \diagdown & \diagdown \\ R^4 & R^4 \end{array}$$

where

A, O, $R^3$, Y and d are as defined above, and $R^4$ is a straight-chain alkyl radical having 5 to 27 carbon atoms, preferably having 5 to 17 carbon atoms, particularly preferably an n-pentyl, n-heptyl, n-nonyl or n-undecyl radical.

$R^4$ is preferably selected from n-pentyl, n-heptyl, n-octyl, n-nonyl, n-undecyl, n-tridecyl, n-pentadecyl and n-heptadecyl, particularly preferably from n-pentyl, n-heptyl, n-nonyl and n-undecyl. Within a molecule of the formula IV, $R^4$ can also be various radicals from those mentioned.

The compounds of the formulae I and IV according to the invention and the compounds moreover coming under the formulae Ia and IVa described in the following have the desired properties as solubilizers, emulsifiers and/or detergents.

The invention thus further relates to the use of a compound of the formula Ia $$(\text{H}\odot)_{a-b}A(\odot W)_b \quad \text{(Ia)}$$

where

A, O and b are as defined in the case of the compounds of the formula I, and

W is a radical of the formula IIa $$-\overset{O}{\underset{\|}{C}}-R^3-\overset{O}{\underset{\|}{C}}-O-\left[A(OY)_{a-2}-O-\overset{O}{\underset{\|}{C}}-R^3-\overset{O}{\underset{\|}{C}}-O\right]_e-A(OY)_{a-1}$$
$$\begin{array}{cc} R^2(Z)c & R^2(Z)c \\ | & | \\ R^1 & R^1 \end{array}$$

where

A, O, a, $R^1$, $R^2$, $R^3$, c, Z and = are defined as in the case of the compounds of the formula I;

where Y is a hydrogen atom or a radical W, which is as defied above; and e is an integer $\geq 0$, preferably 0–100, particularly preferably 0–20, very particularly preferably 0–4;

as a solubilizer, emulsifier and/or detergent.

Particularly preferred here is the corresponding use of a compound of the formula IVa where A, O, $R^3$, Y and e are as defined in the case of the compounds of the formula Ia; and

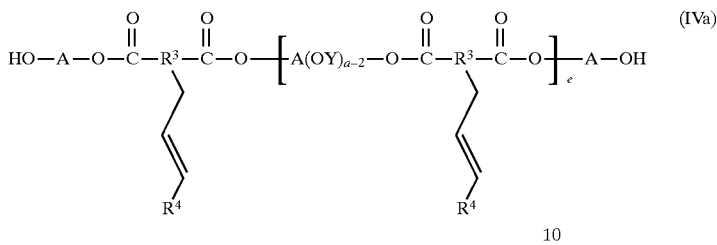

(IVa)

$R^4$ is as defined in the case of the compounds of the formula IV.

With respect to the preferred embodiments of the radicals $R^1$ and $R^2$ in the compounds of the formulae Ia and IVa, what has been said above for the compounds of the formula I or IV applies.

In the compounds of the formulae I, Ia, IV and IVa, the radical A is preferably selected from glycerol, oligomeric glycerol having up to 20 glycerol units, such as diglycerol, triglycerol, tetraglycerol, pentaglycerol, hexaglycerol, octaglycerol, decaglycerol, and also from pentaerythritol and trimethylolpropane and sugar alcohols or anhydrosugar alcohols, such as, in particular, sorbitol, mannitol, adonitol, arabitol, xylitol, dulcitol, isosorbide, sorbitan and erythritol. Glycerol and the oligomeric glycerols mentioned are particularly preferred. Oligomeric glycerols having 2 to 10 glycerol units are very particularly preferred.

In the compounds of the formulae I, Ia, IV and IVa, $R^3$ is preferably an ethylene radical.

The compounds of the formulae Ia and IVa are generally used as solubilizers, emulsifiers and/or detergents in aqueous and aqueous/ethanolic systems which contain at least one substance which is poorly soluble or insoluble therein. Use is preferred, for example, in cosmetic compositions, in detergents and cleaners, in pharmaceutical compositions, in dietetic and nondietetic foodstuffs and/or in crop protection compositions.

The present invention thus further relates to a cosmetic composition, comprising at least one substance which is poorly soluble or insoluble in water and, if appropriate, customary auxiliaries and/or additives, the cosmetic composition comprising at least one of the abovementioned compounds of the formula Ia or IVa, in particular, as a solubilizer and/or emulsifier.

The compounds of the formulae Ia and IVa are particularly suitable here for the solubilization of poorly soluble cosmetic bases, in particular cosmetic oils. They have an excellent solubilizing power for fatty oils such as groundnut oil, jojoba oil, coconut oil, almond oil, olive oil, palm oil, castor oil, soybean oil or wheatgerm oil; or for ethereal oils such as templin oil, lavender oil, rosemary oil, pine-needle oil, eucalyptus oil, peppermint oil, sage oil, bergamot oil, terpentine oil, melissa oil, juniper oil, lemon oil, aniseed oil, cardamom oil, camphor oil etc., for cosmetic bases such as galaxolide, vanillin, menthol, hexylcinnamaldehyde, benzyl acetate, lysmeral, linalool, geraniol, linalyl acetate, etc.; or for mixtures of these oils and bases.

The cosmetic compositions according to the invention are solubilizates based on water or water/alcohol. The compounds of the formulae Ia and IVa are preferably employed as solubilizer and/or emulsifier in the weight ratio from 0.01:1 to 10:1, preferably from 0.1:1 to 6:1, to the cosmetic base.

Other auxiliaries and/or additives can additionally be present in the cosmetic compositions according to the invention. These can be typical nonionic, cationic, anionic or amphoteric surfactants, for example alkyl polyglycosides, fatty alcohol sulfates, fatty alcohol ether sulfates, alkanesulfonates, fatty alcohol ethoxylates, fatty alcohol phosphates, fatty alcohol ether sulfonates, alkylbetaines, sorbitan esters, POE sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurinates, citric acid esters, silicone copolymers, fatty acid polyglycol esters etc. These customarily act as coemulsifiers. Other constituents which can be added are natural or synthetic compounds, such as, for example, lanolin derivatives, cholesterol derivatives, isopropyl myristate, isopropyl palmitate, and also electrolytes, colorants, preservatives, acids (for example lactic acid or citric acid) and bases.

Examples of cosmetic compositions according to the invention which may be mentioned are bath additive preparations such as bath oils, as well as aftershave/preshave lotions, face lotions, mouthwashes, hair lotions, eau de Cologne, eau de toilette etc.

A further object according to the invention is a detergent or cleaner, in particular for surface-, fabric- and/or body-cleaning, if appropriate comprising customary detergent substances and also customary auxiliaries and/or additives, the detergents or cleaners comprising at least one of the abovementioned compounds of the formula Ia or IVa, in particular, as a detergent.

The detergents and cleaners according to the invention can be used, for example, for cleaning purposes in industry and housekeeping, for washing textiles, for cleaning processes in the foodstuffs sector, in washing-up liquids or for personal hygiene compositions, eg. hair shampoos, hair rinses, shower preparations and foam baths. The cleaner according to the invention preferably contains the detergent of the formula Ia or IVa to from 0.1 to 90% by weight, preferably to from 0.5 to 30% by weight. The cleaners according to the invention can contain any other desired anionic, cationic, nonionic or amphoteric surfactants, eg. the surfactants mentioned above in the case of the cosmetic compositions.

An advantage of the compounds of the formulae Ia and IVa is their low interfacial tension. This contributes to their detergency.

The present invention further relates to pharmaceutical compositions comprising at least one active compound, auxiliary or additive which is poorly soluble or insoluble in water, and, if appropriate, other active compounds, auxiliaries and/or additives, the pharmaceutical composition comprising at least one of the abovementioned compounds of the formula Ia or IVa as set forth in one of claims 5 to 8, in particular, as a solubilizer and/or emulsifier.

The active compound which is poorly soluble or insoluble in water can be, for example, an oil-soluble vitamin or vitamin derivative. In particular, the vitamins of the A, D, E and K series may be mentioned here.

In the pharmaceutical compositions according to the invention, the compounds of the formulae Ia and IVa in particular act as a solubilizer or emulsifier, such that aqueous or aqueous/alcoholic active compound solutions can be prepared for oral administration or topical application. The slight intrinsic taste and the only weak intrinsic odor of the compounds mentioned are moreover a great advantage here.

In addition to the vitamins mentioned, which according to the invention are solubilized or emulsified by the compounds of the formula Ia or IVa, preferably in aqueous solution, ethereal oils can be solubilized or emulsified particularly readily in aqueous/alcoholic solutions. Other hydrophobic pharmaceutical active compounds (for example miconazole, hexetidine, clotrimazole and benzocaine) can also be converted into aqueous solutions using the compounds mentioned.

The pharmaceutical compositions according to the invention contain compounds of the formula Ia or IVa to from 0.1 to 90% by weight, preferably to from 0.5 to 50% by weight, particularly preferably to from 2 to 25% by weight.

In order, for example, that oil-soluble vitamins afford clear, aqueous solutions, they must first be intimately mixed with the compound of the formula Ia or IVa active as a solubilizer or emulsifier. Other reaction conditions can be seen from the corresponding examples.

The invention furthermore relates to a dietetic or nondietetic foodstuff, comprising at least one foodstuff, auxiliary or additive which is poorly soluble or insoluble in water, the foodstuff comprising at least one of the abovementioned compounds of the formula Ia or IVa, in particular as a solubilizer and/or emulsifier. Such foodstuffs contain the compounds mentioned to from 0.01 to 30% by weight, preferably to from 0.1 to 10% by weight. The solubilizing and emulsifying properties of the compounds of the formula Ia or IVa, in particular with foodstuffs which are otherwise poorly soluble or insoluble, provide, for example, the conditions for effective utilization of the foodstuffs. For example, foodstuffs, in particular energy drinks, for competitive sportsmen are conceivable here. These advantageous properties of the compounds mentioned can also be utilized in animal feed and in veterinary pharmaceuticals, for example in connection with the use of fatty substances in mixed feed or for the production of cod liver oil emulsions in veterinary medicine.

Finally, the invention relates to a crop protection composition comprising at least one active compound, auxiliary or additive which is poorly soluble or insoluble in water, wherein the crop protection composition comprises at least one of the abovementioned compounds of the formula Ia or IVa, in particular as a solubilizer and/or emulsifier. Crop protection compositions frequently contain hydrophobic active compounds which can be utilized better in aqueous systems, such as spray mixtures, due to the solubilizing or emulsifying properties of the compounds mentioned. The compounds of the formula Ia or IVa are employed in crop protection compositions, preferably to from 0.1 to 80% by weight, particularly preferably to from 1 to 50% by weight.

Generally speaking, the compounds of the formula Ia or IVa can be advantageously employed in particular where good action as a solubilizer or emulsifier is desired.

Use according to the invention of the bisesters of the formula Ia or IVa mentioned in the examples is further preferred.

The invention further relates to a process for preparing compounds of the formula I or Ia, a compound of the formula V

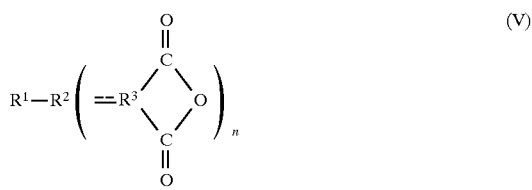

where
$R^1$, $R^2$ and $R^3$ are as defined in the case of the compounds of the formula I or Ia, and
n is 1 or 2; or
a compound of the formula VI

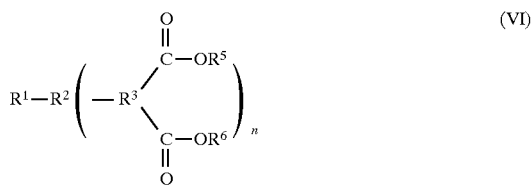

where
$R^1$, $R^2$, $R^3$ and n are as defined above, and
$R^5$ and $R^6$ in each case independently of one another are a hydrogen atom or an alkyl radical, in particular a $C_1$–$C_4$-alkyl radical;
being reacted with a monomeric polyalcohol or an oligomeric polyalcohol of the formula VII

where A, O and a are as defined above, in the presence of at least one catalyst or of a mixture of a number of catalysts, the catalyst or the catalysts preferably being a weakly acidic catalyst, a Lewis acid catalyst and/or a basic catalyst.

The process is an esterification reaction. It was surprisingly found that the use of standard esterification catalysts, such as p-toluenesulfonic acid, sulfuric acid, potassium hydrogen sulfate or hydrochloric acid, are only of limited suitability for this reaction, as they frequently lead to highly viscous products which are no longer stirrable, thus cannot be completely reacted and are not usable according to the invention.

According to the invention, on the contrary the use of the following catalysts is preferred, with which the disadvantages described above do not result and which give conversions of from 95 to 100% based on the dicarboxylic acid derivatives of the formulae V and VI employed:

weakly acidic catalysts: for example phosphorous acid, hypophosphorous acid, phosphoric acid, phosphonic acid and boric acid;

Lewis acid catalysts: for example aluminum chloride, boron trifluoride, an orthotitanate, preferably tetraethyl orthotitanate or tetrabutyl orthotitanate, tin dioxide and tin dibutyldilaurate;

basic catalysts: for example sodium methoxide, sodium ethoxide, sodium carbonate, potassium carbonate, potassium tert-butoxide, sodium hydroxide, potassium hydroxide, lithium hydroxide, calcium hydroxide, magnesium oxide, potassium phosphate.

The catalysts mentioned can be employed on their own or preferably as a mixture. A particularly preferred catalyst mixture comprises an orthotitanate, preferably tetraethyl or tetrabutyl orthotitanate, potassium carbonate and hypophosphorous acid. A catalyst mixture of this type leads, with high conversions of the dicarboxylic acid derivatives of the formula V or VI, to pale products which can be used advantageously according to the invention.

In the process according to the invention, at least 4 mole equivalents of OH groups of the oligomeric polyalcohol of the formula VII are furthermore preferably employed per mole equivalent of a compound of the formula V or VI. The polyalcohol can also be employed in a large excess. Residual polyalcohol can be removed after the reaction by phase separation.

Customarily, the reaction takes place in the presence of the catalysts mentioned with removal of the water of reaction by distillation. The first reaction stage leads to the hemiester which, under the required reaction conditions (suitable catalyst, elevated temperature, if appropriate vacuum, distillative removal of the water of reaction or of resultant alcohol), then reacts to give the bisester of the formula I or Ia.

Use of the catalysts in an amount of from 0.1 to 5% by weight, preferably from 0.5 to 2% by weight, based on the weight of the sum of the starting substances, is optimal. The reaction can be carried out in solvents or without solvent. The solvents should customarily be polar and inert under the reaction conditions. Suitable solvents are, for example, N,N-dimethylformamide, N,N-dimethylacetamide, N-methylpyrrolidone, diglyme, dimethylethylene glycol, tetrahydrofuran, dioxane, acetonitrile, nitromethane, hexamethylphosphoramide, dimethyl sulfoxide, ethylene carbonate, propylene carbonate, tetrahydrothiophene 1,1-dioxide. The solvents can be distilled off during the reaction or after completion of the reaction.

As a rule, the reaction is carried out at from 1 mbar to normal pressure, preferably from 20 mbar to normal pressure, and at from 60° to 250° C., preferably from 120° to 200° C. The water of reaction formed should be removed during the reaction. Depending on the conditions, the reaction times are from approximately 2 to approximately 20 hours. Checking of the reaction is carried out by means of IR spectroscopy and/or by means of the determination of the acid number.

The compounds of the formula I or Ia according to the invention can also be defined by the process used for their preparation.

The invention thus further relates to a compound which is obtainable on the basis of the process described above.

The reaction does not have to take place completely in order to yield a reaction product to be employed according to the invention. Up to 10% of unreacted monoesters of the compounds according to the invention can be tolerated. The incompletely reacted monoesters can also be neutralized using bases and then be present as a salt which can be used together with the completely reacted bisesters.

The actions according to the invention as a solubilizer, emulsifier and/or detergent substance are achievable both using the individual compounds of the formula Ia or IVa (monomers or oligomers) and using mixtures thereof. The individual compounds can be obtained, for example, by chromatographic separation of the industrial reaction mixtures which are formed as a product of the process according to the invention, eg. by preparative gel-permeation chromatography (GPC). For cost reasons, however, the reaction mixtures obtained are preferably employed. By variation of the preparation conditions, eg. excess of alcohol, the molar ratio of the products formed can be varied.

The compounds of the formulae V and VI used as starting substances for the synthesis of the compounds of the formulae I and Ia can be prepared in a known, customary manner.

For example, alkenylsuccinic anhydrides can be prepared by means of an ene reaction of maleic anhydride with appropriate olefins. The degree of maleation here can be up to 200%, ie. by double ene reaction 2 succinic acid radicals are bonded to the original olefin, which leads to compounds of the formula I or Ia where c=1. Alkylsuccinic acids and anhydrides can be prepared, for example, by hydrogenation of the corresponding alkenylsuccinic anhydrides. Various isomeric products can be formed in the ene reaction, which is shown by way of example with the aid of the following reaction scheme for the preparation of succinic acid derivatives:

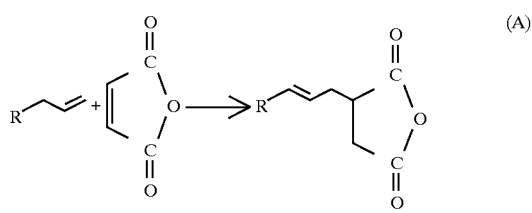
(A)

As a result of a double ene reaction, the monoalkenylsuccinic anhydride (A) can react further to give the isomeric products (B) and (C), which are bisalkenylsuccinic anhydrides.

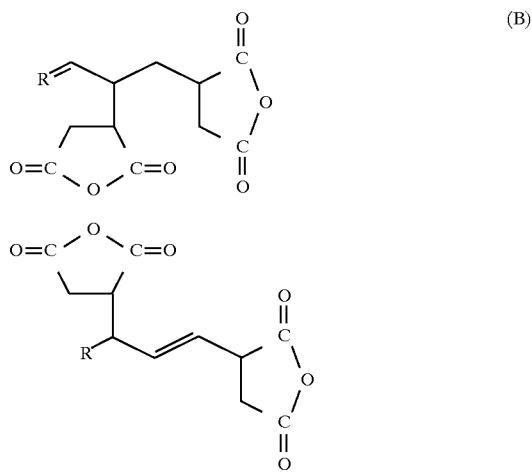
(B)

The compounds of the formulae (A), (B) and (C) are here exemplary of the possible cis/trans isomers which can be formed with respect to the double bond.

In a reaction of this type, the compounds of the formula (A) are in general formed as the main product, while the compounds of the formulae (B) and (C) are only formed to about 5% in each case. By the choice of suitable reaction conditions, the ratio of the individual products to one another can be shifted. The products mentioned can be employed as starting substances in the process according to the invention as a technical mixture or, after their isolation, in pure form.

Alkenylsuccinic acid esters can be obtained by esterification of the alkenylsuccinic anhydrides with alcohols such as methanol, ethanol, propanol, i-propanol, butanol or i-butanol. This esterification can be acid-catalyzed. An excess of alcohol, which can then be distilled off again, is favorable.

The alkylmalonic acid esters or anhydrides and the alkylglutaric acid esters or anhydrides of the formula VI can be prepared by reaction of the corresponding malonic or glutaric acid derivatives with alkyl halides, alkyl sulfates or alkyl tosylates with basic catalysis, such as, for example, an alkoxide.

The alkenylmalonic acid and -glutaric acid esters or anhydrides can be prepared in a similar manner to the alkyimalonic acid derivatives or alkylglutaric acid derivatives by use of appropriate alkenyl halides, alkenyl sulfates or alkenyl tosylates.

The corresponding dicarboxylic acid derivatives of the formula VI are formed from the esters by hydrolysis. The corresponding monocarboxylic acid monoester derivatives are obtainable by partial hydrolysis.

By reaction of the said esters with aldehydes under basic catalysis, the corresponding alkylidene derivatives are obtained. These can likewise be hydrogenated to give the alkyl derivatives.

Synthesis examples for compounds of the formula I or Ia and use examples for compositions according to the invention are shown in the following.

IV. EXAMPLES

The subjects of the present invention are illustrated by the following examples, in which other preferred individual features of the invention are described.

1. Synthesis Examples

Synthesis examples for some of the compounds of the formula I or II according to the invention and for comparison compounds of the prior art are shown below.

General Preparation Processes

Variant A:

An alkenylsuccinic anhydride is initially introduced together with a polyalcohol. At the same time, 0.5% by weight of hypophosphorous acid is added as a catalyst. The mixture is heated to 180° C. under a moderate stream of nitrogen. The water of reaction is distilled off with stirring. The course of the reaction is determined by means of the acid number. If the acid number is <10 mg of KOH/g, the reaction mixture is cooled and the residual acid groups are neutralized using NaOH.

Variant B:

An alkenylsuccinic anhydride is initially introduced together with a polyalcohol. At the same time, 1% by weight of sodium methoxide is added as a catalyst. The mixture is heated to 120° C. under a moderate stream of nitrogen and a vacuum of 20 mbar is applied. The water of reaction is distilled off with stirring. The course of the reaction is determined by means of the acid number. If the acid number is <10 mg of KOH/g, the reaction mixture is cooled and the residual acid groups are neutralized using NaOH.

Variant C:

A polyalcohol is initially introduced together with the catalyst mixture (0.5% by weight of hypophosphorous acid, 0.5% by weight of tetraethyl orthotitanate and 0.2% by weight of sodium carbonate). The alkenylsuccinic anhydride is added dropwise at 80° C. in the course of one hour. The reaction mixture is then heated to 180° C. under a moderate stream of nitrogen. The water of reaction is distilled off with stirring. The course of the reaction is checked by means of the acid number. If the acid number is <10 mg of KOH/g, the residual acid groups are neutralized using NaOH. The still-warm reaction mixture is filtered and then cooled.

Variant D (Preparation of Comparison Compounds):

An alkenylsuccinic anhydride is initially introduced together with a polyalcohol. The mixture is heated to 80° C. and stirred under a moderate stream of nitrogen. The course of the reaction is monitored by IR spectroscopy. After decrease of the anhydride bands at 1780 and 1830 cm$^{-1}$, the reaction mixture is cooled. The free acid groups can be neutralized using NaOH.

Example 1

Preparation of a mixture of monomeric and oligomeric bisesters, starting from a C8- and a C10-alk-2-en-1-ylsuccinic anhydride (molar ratio is C8:C10=1:1) and polyglycerol (mean molecular weight of the polyglycerol=201 g/mol; molar ratio of alkenylsuccinic anhydride to polyglycerol 1:2). Preparation was carried out using the process of variant A; the acid number of the final product was 7.2 mg of KOH/g.

Example 2

Preparation of a mixture of monomeric and oligomeric bisesters, starting from a C10- and a C12-alk-2-en-1-ylsuccinic anhydride (molar ratio C10:C12=0.5:1) and polyglycerol (mean molecular weight of the polyglycerol= 201 g/mol; molar ratio of alkenylsuccinic anhydride to polyglycerol 1:2). Preparation was carried out by means of the process of variant A; the acid number was 7.5 mg of KOH/g.

Example 3

Preparation of a mixture of monomeric and oligomeric bisesters, starting from a C12- and a C14-alk-2-en-1-ylsuccinic anhydride (molar ratio C12:C14=1:0.5) and polyglycerol (mean molecular weight of the polyglycerol= 201 g/mol; molar ratio of alkenylsuccinic anhydride to polyglycerol 1:2). Preparation was carried out using the process of variant A; the acid number was 7.6 mg of KOH/g.

Example 4

Preparation of a mixture of monomeric and oligomeric bisesters, starting from a C12- and a C14-alk-2-en-1-ylsuccinic anhydride (molar ratio C12:C14=1:0.5) and pentaglycerol (mean molecular weight of the pentaglycerol= 388 g/mol; molar ratio of alkenylsuccinic anhydride to polyglycerol 1:2). Preparation was carried out by means of the process of variant A; the acid number was 3.9 mg of KOH/g.

Example 5

Preparation of a mixture of monomeric and oligomeric bisesters, starting from a dec-2-en-1-ylsuccinic anhydride and mannitol (molar ratio of alkenylsuccinic anhydride to mannitol 1:2). Preparation was carried out by means of the process of variant B; the acid number was 13.5 mg of KOH/g.

Example 6

Preparation of a mixture of monomeric and oligomeric bisesters, starting from a dodec-2-en-1-ylsuccinic anhydride and sorbitol (molar ratio of alkenylsuccinic anhydride to sorbitol 1:2). Preparation was carried out by means of the process of variant B; the acid number was 15 mg of KOH/g.

Example 7

Preparation of a mixture of monomeric and oligomeric tetraesters, starting from a C12- and a C14-alkenyl-bis-succinic anhydride (molar ratio C12:C14=1:0.5) and glycerol (molar ratio of alkenylbis-succinic anhydride to glycerol 1:4). Preparation was carried out by means of the process of variant A; the acid number was 17 mg of KOH/g.

Example 8

Preparation of a mixture of monomeric and oligomeric bisesters, starting from a dec-2-en-1-ylsuccinic anhydride and polyglycerol (mean molecular weight of the polyglycerol=201 g/mol; molar ratio of alkenylsuccinic anhydride to polyglycerol 1:2). Preparation was carried out by means of the process of variant C; the acid number was 7.1 mg of KOH/g.

Example 9

Preparation of a mixture of monomeric and oligomeric bisesters, starting from an octadec-2-en-1-yl- succinic anhydride and decaglycerol (mean molecular weight of the polyglycerol=750 g/mol; molar ratio of alkenylsuccinic anhydride to polyglycerol 1:2). Preparation was carried out by means of the process of variant A; the acid number was 9.1 mg of KOH/g.

Example 10 (Comparison Compound)

Preparation of a monoester, starting from a C10- C12-alk-2-en-1-ylsuccinic anhydride (molar ratio C10:C12= 0.5:1) and polyglycerol (mean molecular weight of the polyglycerol=201 g/mol; molar ratio of alkenylsuccinic anhydride to polyglycerol 1:2). Preparation was carried out by means of the process of variant D; the acid number was 126 mg of KOH/g.

Example 11 (Comparison Compound)

Preparation of the sodium salt of the compound from Example 10 (mean molecular weight of the polyglycerol= 201 g/mol; molar ratio of alkenylsuccinic anhydride to polyglycerol 1:2). Preparation was carried out using the process of variant D; after neutralization the acid number was <1 mg of KOH/g.

2. Use Examples 2.1 Efficacy of the Compounds According to the Invention:

Table 1 shows the hard water stability and the interfacial tensions to selected oils from the cosmetics and cleaning sector.

For use of the products as detergents in cleaners, the water hardness stability is an important criterion. The solubility in water of 20° dH was tested at 25° C.; the concentration was 1 g/l.

The emulsifying or solubilizing power of the substances according to the invention is characterized by the interfacial tension between the aqueous solution (dist. water) of the substance and an oil phase. Measurement was carried out by means of a spinning drop tensiometer.

TABLE 1

| Product from Synthesis Example No. | Solubility in $H_2O$ (20° C.) | Solubility in $H_2O$ 20° dH (25° C.) | Interface tensions[a] to | |
|---|---|---|---|---|
| | | | Olive oil | Rosemary oil |
| 1 | clear | clear | 0.93 mN/m | 0.18 mN/m |
| 2 | clear | clear | 0.66 mN/m | 0.15 mN/m |
| 3 | clear | clear | 0.88 mN/m | 0.12 mN/m |
| 4 | clear | clear | | |
| 5 | clear | trace of turbidity | 0.93 mN/m | 1.3 mN/m |
| 6 | clear | trace of turbidity | 1.34 mN/m | 2.28 mN/m |
| 7 | clear | trace of turbidity | | |
| 8 | clear | clear | 0.75 mN/m | 0.16 mN/m |
| 9 | clear | clear | | |
| 10 | slightly turbid | turbid | 2.8 mN/m | 2.0 mN/m |

TABLE 1-continued

| Product from Synthesis Example No. | Solubility in $H_2O$ (20° C.) | Solubility in $H_2O$ 20° dH (25° C.) | Interface tensions[a] to | |
|---|---|---|---|---|
| | | | Olive oil | Rosemary oil |
| 11 | clear | turbid | 2.3 mN/m | 2.9 mN/m |

[a]Concentration = 1 g/l, measured at 25° C.

It is seen that the compounds of Synthesis Examples 1 to 9 according to the invention have a better hard water stability and/or substantially lower interfacial tensions than the compounds of Synthesis Examples 10 and 11, which serve for comparison and are disclosed in JP 05 125 014. This makes possible the preferred use of the compounds according to the invention as a detergent and/or as an emulsifier/solubilizer.

2.2 Preparation of Solubilizates of Cosmetic Oils as Examples of Cosmetic Compositions According to the Invention The compounds of the formulae I and II can be employed as a pure substance or as an aqueous solution. Customarily, from 1 to 6 g (based on the active substance) of the corresponding bisester are intimately mixed with 1 g of the ethereal oil or perfume oil used in each case, for example by means of a magnetic stirrer. While stirring continuously, demineralized water is slowly added to 100 g using a burette. If required, the mixtures are warmed to from 60° to 80° C.

A widespread method for finding the optimum solubilization effect of amphiphilic compounds is turbidity titration, as has been described, for example, in A. Domsch, Die Kosmetischen Präparate (Cosmetic Preparations), 4th edition of the work started by G. A. Novak, Volume II, W äBrige und tensidhaltige Formulierungen (Aqueous and Surfactant-containing Formulations).

Use Examples 1 to 10 show the advantageous properties of the cosmetic compositions according to the invention, while Comparison Examples 1 to 4 confirm the disadvantages with respect to stability in the case of comparison compounds.

Use Example 1

1 g of oral hygiene aromatic oil Dragoco ZM 0065 and 3 g of the compound of Synthesis Example 1 are mixed with 96 g of water and stirred at room temperature for 5 minutes. A clear solubilizate is obtained which is stable for a long period.

Use Example 2

1 g of lavender oil and 3 g of the compound of Synthesis Example 2 are mixed with 96 g of water and stirred at room temperature for 5 minutes. A clear solution which is stable for a long period is obtained.

Use Example 3

1 g of rosemary oil and 3 g of the compound of Synthesis Example 2 are mixed with 96 g of water and stirred at room temperature for 5 minutes. A clear solution is obtained which is stable for a long period.

Use Example 4

1 g of pine-needle oil and 3 g of the compound of Synthesis Example 2 are mixed with 76.8 g of water and 19.2 g of ethanol and stirred at room temperature for 5 minutes. A clear solution is obtained which is stable for a long period.

Use Example 5

1 g of lavender oil and 3 g of the compound of Synthesis Example 3 are mixed with 76.8 g of water and 19.2 g of ethanol and stirred at room temperature for 5 minutes. A clear solution is obtained which is stable for a long period.

Use Example 6

1 g of templin oil and 3 g of the compound of Synthesis Example 3 are mixed with 96 g of water and stirred at room temperature for 5 minutes. A clear solution is obtained which is stable for a long period.

Use Example 7

1 g of rosemary oil and 3 g of the compound of Synthesis Example 4 are mixed with 76.8 g of water and 19.2 g of ethanol and stirred at room temperature for 5 minutes. A slightly turbid solution is obtained which is stable for a long period.

Use Example 8

1 g of Blue Water perfume oil (Haarmann & Reimer) and 3 g of the compound of Synthesis Example 5 are mixed with 76.8 g of water and 19.2 g of ethanol and stirred at room temperature for 5 minutes. A clear solution is obtained which is stable for a long period.

Use Example 9

1 g of oral hygiene oil (Dragoco ZM 0065) and 3 g of the compound of Synthesis Example 6 are mixed with 96 g of water and stirred at room temperature for 5 minutes. A clear solution is obtained which is stable for a long period.

Use Example 10

1 g of rosemary oil and 3 g of the compound of Synthesis Example 7 are mixed with 96 g of water and stirred at room temperature for 5 minutes. A clear solution is obtained which is stable for a long period.

Use Example 11

1 g of pine-needle oil and 3 g of the compound of Synthesis Example 8 are mixed with 96 g of water and stirred at room temperature for 5 minutes. A clear solution is obtained which is stable for a long period.

Comparison Example 1

1 g of rosemary oil and 3 g of the compound of Synthesis Example 10 are mixed with 96 g of water and stirred at room temperature for 5 minutes. A milky emulsion is obtained which has already separated after 24 h.

Comparison Example 2

1 g of rosemary oil and 3 g of the compound of Synthesis Example 11 are mixed with 96 g of water and stirred at room temperature for 5 minutes. A milky emulsion is obtained which has already separated after 24 h.

Comparison Example 3

1 g of oral hygiene aromatic oil (Dragoco ZM 0065) and 3 g of the compound of Synthesis Example 10 are mixed with 76.8 g of water and 19.2 g of ethanol and stirred at room temperature for 5 minutes. A milky emulsion is obtained which has already separated after 24 h.

Comparison Example 4

1 g of oral hygiene aromatic oil (Dragoco ZM 0065) and 3 g of the compound of Synthesis Example 11 are mixed with 76.8 g of water and 19.2 g of ethanol and stirred at room temperature for 5 minutes. A milky emulsion is obtained which has already separated after 24 h.

2.3 Preparation of Solubilizates of Oil-Soluble Vitamins as an Example of a Pharmaceutical Composition According to the Invention

Use Example 1

5 g of vitamin A palmitate are mixed with 25 g of the compound of Synthesis Example 9 and warmed to from 60° to 65° C. 70 g of water likewise warmed to from 60° to 65° C. are very slowly incorporated into this mixture with intimate stirring. A clear solubilizate is obtained in this process. If the addition of water is carried out too rapidly, the solution may become turbid.

We claim:

1. A compound of the formula I

where

A is the radical of a monomeric polyalcohol or of an oligomeric polyalcohol which consists of up to 20 monomers linked to one another via end bonds, the monomeric polyalcohol or the monomer of the oligomeric polyalcohol being an alcohol which has at least 3 carbon atoms and a OH groups;

a is $\geq 2$;

⊙ is in each case an oxygen atom of one of the OH groups of the radical A;

X is a radical of the formula II

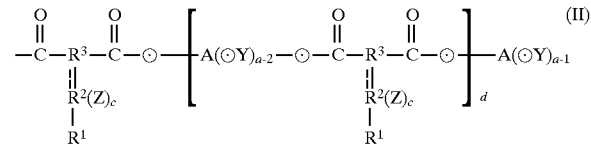

where

A, ⊙ and a are as defined above;

Y is a hydrogen atom, or a radical X, which is defined as above;

$R^1$ is a straight-chain or branched alkyl or alkenyl radical having at least 8 carbon atoms;

$R^2$ is a carbon—carbon bond or a straight-chain or branched alkylene or alkenylene radical;

where $R^1$ and $R^2$ together have up to 30 carbon atoms;

$R^3$ is a methylene, ethylene or n-propylene radical,

--- is a single or double bond;

Z is a radical of the formula III

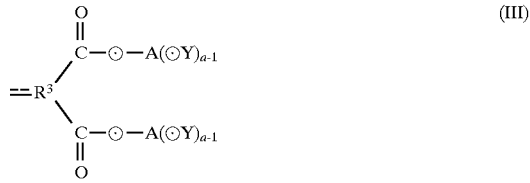

where

A, ⊙, a, Y and --- are as defined above;

c is 0 or 1;

d is an integer $\geq 1$, and b is an integer which is at least 1 and at most a, which is as defined above.

2. A compound of the formula I as claimed in claim 1, wherein $R^1$ and $R^2$ together are a straight-chain alkyl or an alkenyl radical with a total of 8 to 20 carbon atoms; and when --- is a double bond, $R^1$ and $R^2$ have no additional double bonds; and when --- is a single bond, $R^1$ and $R^2$ in total have 1 double bond.

3. A compound as claimed in claim 1, which has the formula IV:

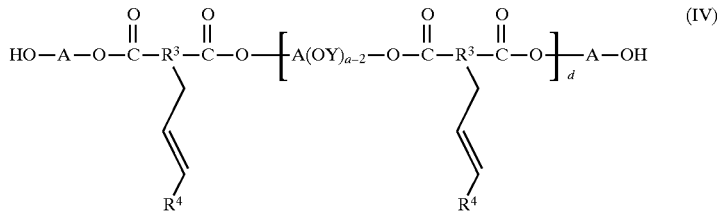

where

A, ⊙, $R^3$, Y and d are as defined above, and $R^4$ is a straight-chain alkyl radical having 5 to 27 carbon atoms.

4. A compound as claimed in claim 1, wherein the radical A is selected from the group consisting of glycerol, oligomeric glycerol having up to 20 glycerol units, pentaerythritol, trimethylopropane, sugar alcohols and anhydrosugar alcohols.

5. The method of solubilizing, emulsifying, or cleaning a substance, comprising contacting the substance with a compound of the formula Ia

where

A, ⊙ and b are as defined in claim 1; and W is a radical of formula IIa:

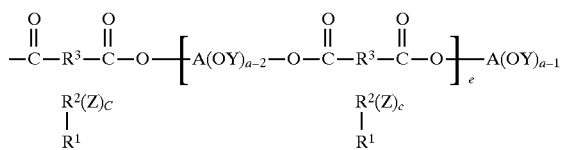

where

A, ⊙, $R^1$, $R^2$, $R^3$, C, Z and --- are defined as in claim 1;

Y is a hydrogen atom or a radical W, which is as defined above; and e is an integer $\geq 0$.

6. The method as claimed in claim 5, wherein $R^1$ and $R^2$ together being a straight-chain alkyl or alkenyl radical with a total of 8 to 20 carbon atoms; and when --- is a double bond, $R^1$ and $R^2$ have no additional double bonds; and when --- is a single bond, $R^1$ and $R^2$ in total have 1 double bond.

7. The method as claimed in claim 5, wherein the compound has the formula IVa:

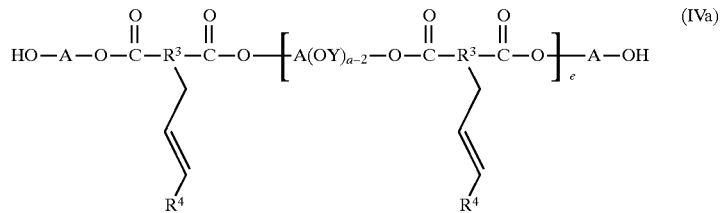

where

A, ⊙, $R^3$, Y and e are as defined in claim 5; and $R^4$ is a straight-chain alkyl radical having 5 to 27 carbon atoms.

8. The method as claimed in claim 5, wherein the radical A is selected from the group consisting of glycerol, oligomeric glycerol having up to 20 glycerol units, pentaerythritol, trimethylopropane, and sugar alcohols and anhydrosugar alcohols.

9. The method as claimed in claim 5, wherein the substance is a cosmetic composition.

10. The method as claimed in claim 5, wherein the substance is a detergent or cleaner composition.

11. The method as claimed in claim 5, wherein the substance is a pharmaceutical composition.

12. The method as claimed in claim 5, wherein the substance is a dietetic or nondietetic foodstuff.

13. The method as claimed in claim 5, wherein the substance is a crop protection composition.

14. A cosmetic composition, comprising (a) at least one substance which is poorly soluble or insoluble in water, (b) optionally, customary auxiliaries and/or additives, and (c) at least one compound of the formula Ia or IVa as set forth in claim 5.

15. A detergent and/or cleaner, comprising at least one compound of the formula Ia or IVa as set forth in claim 5, optionally, customary detergents and customary auxiliaries and/or additives.

16. A pharmaceutical composition comprising (a) at least one active compound, auxiliary or additive which is poorly soluble or insoluble in water, (b) optionally, other active compounds, auxiliaries and/or additives, and (c) at least one compound of the formula Ia or IVa as set forth in claim 5.

17. A dietetic or nondietetic foodstuff, comprising at least one foodstuff, auxiliary or additive which is poorly soluble or insoluble in water, and at least one compound of the formula Ia or IVa as set forth in claim 5.

18. A crop protection composition, comprising at least one active compound, auxiliary or additive which is poorly soluble in water and at least one compound of the formula Ia or Iva as set forth in claim 5.

19. A process for preparing a compound of the formula I or Ia as claimed in claim 1, which comprises reacting a compound of the formula V

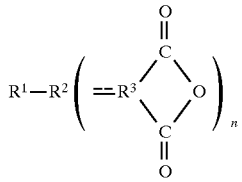 (V)

where $R^1$, $R^2$ and $R^3$ are defined in claim 1, and n is 1 or 2; or a compound of the formula VI:

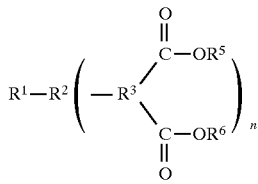 (VI)

where $R^1$, $R^2$, $R^3$ and n are as defined above, and $R^5$ and $R^6$ in each independently of one another are a hydrogen atom or an alkyl radical, with a monomeric polyalcohol or an oligomeric polyalcohol of the formula VII $A(\odot H)_a$ (VII)

where A, $\odot$ and a are as defined in claim 1, in the presence of at least one catalyst or of a mixture of a number of catalysts.

20. A process for preparing a compound of the formula I or Ia as claimed in claim 5, which comprises reacting a compound of the formula V:

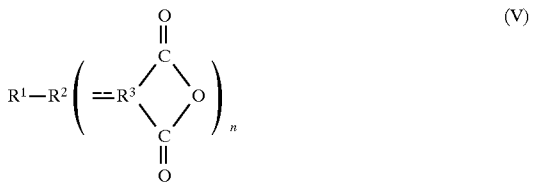 (V)

where $R^1$, $R^2$ and $R^3$ are as defined in claim 5, and n is 1 or 2; or a compound of the formula VI:

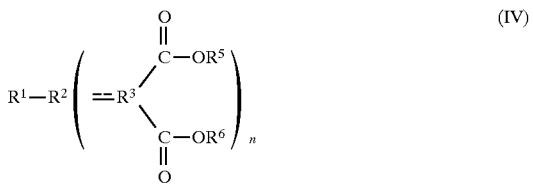 (IV)

where $R^1$, $R^2$, $R^3$ and n are as defined above, and $R^5$ and $R^6$ in each case independently of one another are a hydrogen atom or an alkyl radical, with a monomeric polyalcohol or an oligomeric polyalcohol of the formula VII:

$A(\odot H)_a$ (VII)

where A, $\odot$ and a are as defined in claim 1, in the presence of at least one catalyst or of a mixture of a number of catalysts.

* * * * *